US00PP12231P2

(12) United States Plant Patent
Lemon

(10) Patent No.: US PP12,231 P2
(45) Date of Patent: Nov. 27, 2001

(54) VARIETY OF GERANIUM PLANT NAMED 'PATRIOT WATERMELON'

(75) Inventor: David Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/715,316

(22) Filed: Nov. 17, 2000

(51) Int. Cl.[7] ..... A01H 5/00
(52) U.S. Cl. ..... Plt./330
(58) Field of Search ..... Plt./330, 325

*Primary Examiner*—Amy J. Nelson
*Assistant Examiner*—Kent L. Bell
(74) *Attorney, Agent, or Firm*—Webb Ziesenheim Logsdon Orkin & Hanson, P.C.

(57) ABSTRACT

A new and distinct zonal geranium plant with coral/salmon colored flowers above medium green foliage.

1 Drawing Sheet

BACKGROUND OF THE INVENTION

The present invention comprises a new and distinct cultivar of *Pelargonium×hortorum* known by the varietal name 'Patriot Watermelon' (Oglevee No. 6301, Breeder No. 6DG3252-42). The new variety was discovered in a selected breeding program in Lompoc, Calif. The new variety is a selection from the cross of 'Champion' (unpatented), the female parent, and 'Pink Satisfaction' (U.S. Plant Pat. No. 7,599), the male parent. The new variety was first asexually reproduced by cuttings at Oglevee, Ltd. in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of six weeks from a rooted cutting to flowering in a 10 cm pot. The response time was determined on plants grown in soilless media employing constant fertilizer 200–250 parts per million of nitrogen and potassium in full light. Plants of 'Patriot Watermelon' differ from the plants of the parental cultivars primarily in flower color.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Connellsville, Pa. The color readings were taken indoors under 200–220 foot candles of fluorescent cool white light. Color references are primarily to the R.H.S. Colour Chart of The Royal Horticultural Society of London. Plants described were about 6 weeks old from a rooted cutting.

PLANT

Classification:
*Botanical.*—*Pelargonium×hortorum.*
*Commercial.*—*Zonal geranium.*

Form: Medium mound.
Height: 15.0–17.0 cm from soil to top of foliage.
Growth: Upright, free basal branching.
Strength: Does not require artificial support.
Foliage: Zonation present; stalked leaf attachment.
Rooting time: Roots visible to the outside of an artificial dirt plug in 14–21 days.
Leaves:
*Size.*—Length: 6.0–7.5 cm. Width: 6.0–9.0 cm at widest point.
*Shape.*—Reniform; cordate base.
*Margin.*—Crenate.
*Texture.*—Pubescent.
*Color.*—Upper surface: Green Group 143A with zone of Green Group 137A. Lower surface: Green Group 138B.
*Ribs and veins.*—Venation: Palmate. Color: Yellow-Green Group 145B.
Petioles:
*Color.*—Yellow-Green Group 144A.
*Length.*—4.5–7.0 cm.
Stem:
*Color.*—Yellow-Green Group 144A.
*Internode length.*—2.5–3.5 cm.

THE BUD

Shape just prior to anthesis:
*Overall.*—Elliptical cluster when just showing color.
*Individual bud.*—Elliptical when just showing color.
Size when just showing color:
*Overall.*—4.5–5.0 cm across.
*Individual bud.*—8.0–10.0 mm long; 6.0–7.0 mm wide.
Number of buds per cluster: 27–34.

INFLORESCENCE

Blooming habit: Continuous; free and early flowering.
*Size.*—10.0 cm at widest point on fully open bloom.
*Borne.*—Flowers on umbel; umbel on pedicel; pedicel on peduncle.
Flowers:
*Form.*—Slightly cupped; ruffled.
*Number of flowers per umbel.*—15–22.
*Size.*—2.0–3.5 cm long; 3.5–4.0 cm wide.
*Petals.*—Color: Upper surface: Red Group 43C with some Red Group 43B. Some petals fad to a lighter color of Red Group 43D toward base. Darker veining of Red Group 47C present on some petals. Lower surface: Red Group 43D; some veining of Red Group 47D showing through. Shape: Obovate. Size: 2.3–3.7 cm long; 1.7–2.0 cm across. Margin: Entire. Number per flower: 6–8.

*Texture and appearance.*—Smooth, velvety, reflective.

Tonality from a distance: Clear coral/salmon flowers above medium green foliage.

Petaloids:

*Quantity.*—0–5 per flower.

*Shape.*—Irregular; some twisted, some tubular, some with pollen attached.

*Color.*—Same as petals.

Pedicel:

*Length.*—3.0–3.5 cm.

*Color.*—Ranging from Red Group 46A at top near flower to Yellow-Green Group 144B at base.

Peduncle:

*Length.*—11–13 cm.

*Color.*—Yellow-Green Group 144A.

Disease/pest resistance: No susceptibility to diseases or pests has been noted to date.

Lasting quality: Individual flowers and umbels will last from 7–14 days depending on conditions. Flowering is continuous with new replacing the old throughout the growing season.

REPRODUCTIVE ORGANS

Stamens:

*Anthers.*—0.2 cm long.

*Filaments.*—Length: 0.7–1.0 cm. Color: White with coral tips. Pollen: Golden brown.

Pistils:

*Number.*—One.

*Length.*—0.7–0.9 cm.

*Stigma.*—Number: One; five parted. Color: Red-Purple Group 59B.

*Style.*—Length: 0.4–0.5 cm. Color: Red-Purple Group 59B.

Ovaries:

*Completeness.*—Superior.

*Pubescence.*—Very pubescent.

*Length.*—0.5 cm.

*Width.*—0.2 cm.

*Color.*—Yellow-Green Group 146C.

Fruit: None observed.

GENERAL CHARACTERISTICS

1. Bright coral/salmon flowers above medium green foliage with zoning.

2. Good cutting production and rooting speed.

3. Finishes in 6 weeks while maintaining a neat controlled plant habit.

4. This variety has been trialed both indoors and in the outdoor garden during the 1997, 1998, 1999, and 2000 growing seasons and has performed very well under all weather conditions.

I claim:

1. A new and distinct variety of geranium plant substantially as shown and described.

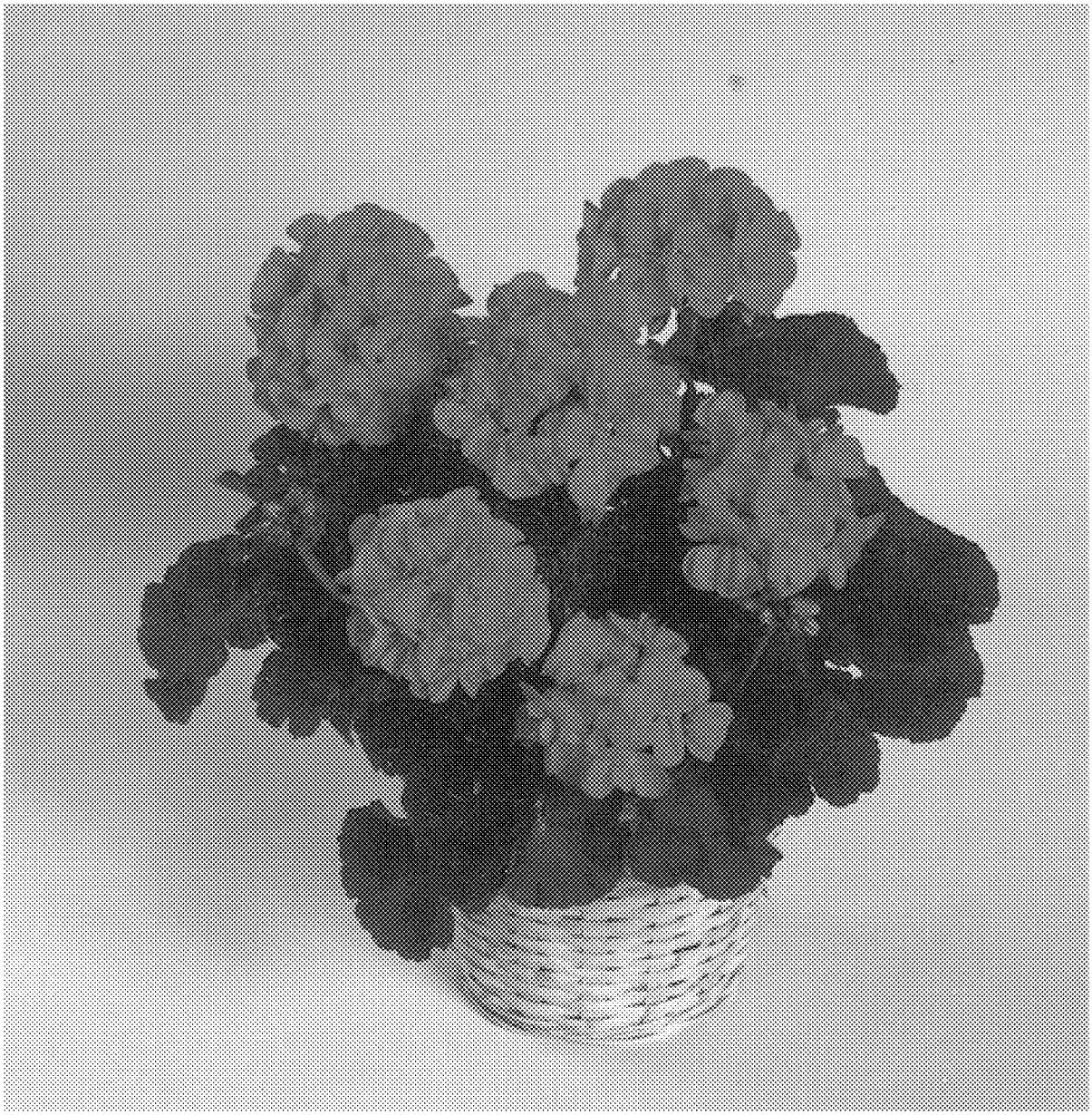

* * * * *